(12) United States Patent
Barchi, Jr. et al.

(10) Patent No.: US 7,790,473 B2
(45) Date of Patent: Sep. 7, 2010

(54) BIOFUNCTIONALIZED QUANTUM DOTS FOR BIOLOGICAL IMAGING

(75) Inventors: Joseph J. Barchi, Jr., Frederick, MD (US); Sergei A. Svarovsky, North Potomac, MD (US)

(73) Assignee: The United States of America as represented by the Department of Health and Human Services, Washington, DC (US)

(*) Notice: Subject to any disclaimer, the term of this patent is extended or adjusted under 35 U.S.C. 154(b) by 1087 days.

(21) Appl. No.: 10/578,405

(22) PCT Filed: Nov. 5, 2003

(86) PCT No.: PCT/US03/34897

§ 371 (c)(1),
(2), (4) Date: May 5, 2006

(87) PCT Pub. No.: WO2005/053649

PCT Pub. Date: Jun. 16, 2005

(65) Prior Publication Data

US 2007/0172427 A1    Jul. 26, 2007

(51) Int. Cl.
*G01N 33/547* (2006.01)
*G01N 33/543* (2006.01)
*G01N 33/24* (2006.01)
*G01N 33/548* (2006.01)

(52) U.S. Cl. .................. 436/532; 436/523; 436/81; 436/529

(58) Field of Classification Search ............... None
See application file for complete search history.

(56) References Cited

U.S. PATENT DOCUMENTS

| 4,795,698 A | 1/1989 | Owen et al. |
| 5,186,827 A | 2/1993 | Liberti et al. |
| 5,200,084 A | 4/1993 | Liberti et al. |
| 5,466,574 A | 11/1995 | Liberti et al. |
| 5,512,332 A | 4/1996 | Liberti et al. |

(Continued)

FOREIGN PATENT DOCUMENTS

EP    0 810 853 B1    8/2004

(Continued)

OTHER PUBLICATIONS

Mitchel et al. Programmed Assembly of DNA functionalized quantum dots. 1999, vol. 121, pp. 8122-8123.*

(Continued)

*Primary Examiner* — Shafiqul Haq
(74) *Attorney, Agent, or Firm* — Woodcock Washburn LLP

(57) ABSTRACT

Novel biofunctionalized quantum dots include a mercaptoalkanoic acid linked to the surface of a nanocrystalline core and a bio-functional group linked to the surface. Biofunctionalized quantum dots are made by a novel synthesis method. Biofunctionalized quantum dots can be used in imaging or therapy applications.

4 Claims, 5 Drawing Sheets

$T_f$-MAA-CdTe

U.S. PATENT DOCUMENTS

| | | | |
|---|---|---|---|
| 5,541,072 A | 7/1996 | Wang et al. | |
| 5,567,326 A | 10/1996 | Ekenberg et al. | |
| 5,698,271 A | 12/1997 | Liberti et al. | |
| 5,795,470 A | 8/1998 | Wang et al. | |
| 5,866,099 A | 2/1999 | Owen et al. | |
| 6,114,038 A | 9/2000 | Castro et al. | |
| 6,120,856 A | 9/2000 | Liberti et al. | |
| 6,194,213 B1 | 2/2001 | Barbera-Guillem | |
| 6,261,779 B1 | 7/2001 | Barbera-Guillem et al. | |
| 6,274,323 B1 | 8/2001 | Bruchez et al. | |
| 6,306,610 B1 | 10/2001 | Bawendi et al. | |
| 6,326,144 B1 | 12/2001 | Bawendi et al. | |
| 6,333,110 B1 | 12/2001 | Barbera-Guillem | |
| 6,365,362 B1 | 4/2002 | Terstappen et al. | |
| 6,444,143 B2 | 9/2002 | Bawendi et al. | |
| 6,444,806 B1 | 9/2002 | Veerapanani et al. | |
| 6,468,808 B1 | 10/2002 | Nie et al. | |
| 6,482,941 B1 | 11/2002 | Khan Riaz et al. | |
| 6,500,622 B2 | 12/2002 | Bruchez, Jr. et al. | |
| 6,544,732 B1 | 4/2003 | Chee et al. | |
| 6,596,555 B2 | 7/2003 | Bensahel et al. | |
| 6,620,627 B1 | 9/2003 | Liberti et al. | |
| 6,623,982 B1 | 9/2003 | Liberti et al. | |
| 6,630,307 B2 | 10/2003 | Bruchez et al. | |
| 6,645,731 B2 | 11/2003 | Terstappen et al. | |
| 6,649,138 B2 | 11/2003 | Adams et al. | |
| 6,653,080 B2 | 11/2003 | Bruchez et al. | |
| 6,682,596 B2 | 1/2004 | Zehnder et al. | |
| 6,710,366 B1 | 3/2004 | Lee et al. | |
| 6,734,420 B2 | 5/2004 | Empedocles et al. | |
| 6,759,235 B2 | 7/2004 | Empedocles et al. | |
| 6,767,702 B2 | 7/2004 | Mirkin et al. | |
| 6,772,070 B2 | 8/2004 | Gilmanshin et al. | |
| 6,774,361 B2 | 8/2004 | Bawendi et al. | |
| 6,777,186 B2 | 8/2004 | Mirkin et al. | |
| 6,788,453 B2 | 9/2004 | Banin et al. | |
| 6,790,455 B2 | 9/2004 | Chu et al. | |
| 6,815,064 B2 | 11/2004 | Treadway et al. | |
| 6,838,243 B2 | 1/2005 | Lai et al. | |
| 6,855,551 B2 * | 2/2005 | Bawendi et al. | 436/6 |
| 2001/0034034 A1 | 10/2001 | Bruchez et al. | |
| 2002/0009728 A1 | 1/2002 | Bittner et al. | |
| 2002/0028457 A1 | 3/2002 | Empedocles et al. | |
| 2002/0090650 A1 | 7/2002 | Empedocles et al. | |
| 2002/0127224 A1 | 9/2002 | Chen | |
| 2002/0144644 A1 | 10/2002 | Zehnder et al. | |
| 2002/0150905 A1 | 10/2002 | Barbera-Guillem et al. | |
| 2003/0008414 A1 | 1/2003 | Nie et al. | |
| 2003/0027214 A1 | 2/2003 | Kamb | |
| 2003/0082237 A1 | 5/2003 | Cha et al. | |
| 2003/0099940 A1 | 5/2003 | Empedocles et al. | |
| 2003/0113709 A1 | 6/2003 | Alivisatos et al. | |
| 2003/0129590 A1 | 7/2003 | Rosenthall et al. | |
| 2003/0129591 A1 | 7/2003 | Rosenthall et al. | |
| 2003/0148544 A1 | 8/2003 | Nie et al. | |
| 2003/0165951 A1 | 9/2003 | Bruchez, Jr. et al. | |
| 2003/0175773 A1 | 9/2003 | Chee et al. | |
| 2004/0007469 A1 | 1/2004 | Ohtsu et al. | |
| 2004/0009911 A1 | 1/2004 | Harris et al. | |
| 2004/0014060 A1 | 1/2004 | Hoheisel et al. | |
| 2004/0023415 A1 | 2/2004 | Sokolov et al. | |
| 2004/0038307 A1 | 2/2004 | Lee et al. | |
| 2004/0158051 A1 | 8/2004 | Ozkan et al. | |
| 2004/0166505 A1 | 8/2004 | Bruchez et al. | |
| 2004/0171039 A1 | 9/2004 | Bruchez et al. | |
| 2004/0178338 A1 | 9/2004 | Empedocles et al. | |
| 2004/0180380 A1 | 9/2004 | Lee et al. | |
| 2004/0197816 A1 | 10/2004 | Empedocles et al. | |
| 2004/0247517 A1 | 12/2004 | Zehnder et al. | |
| 2005/0059031 A1 | 3/2005 | Bruchez et al. | |
| 2005/0214536 A1 | 9/2005 | Schrier et al. | |

FOREIGN PATENT DOCUMENTS

| | | |
|---|---|---|
| WO | WO 2004/039830 A2 | 5/2004 |
| WO | WO 2005/053649 A1 | 6/2005 |
| WO | WO 2005/093422 A2 | 10/2005 |
| WO | WO 2005/093422 A3 | 10/2005 |

OTHER PUBLICATIONS

PCT/US2005/009344 "Notification Concerning Transmittal of Int'l Prelim. Report on Patentability" and "Written Opinion of the ISA", mailed Oct. 5, 2006, U.S. Department of Health and Human Services.

WO 2006/093516 A2, Sep. 8, 2006, The Regents of the University of California.

International Search Report, date, issued in PCT/US2003/34897, mailed Aug. 20, 2004, U.S. Department of Health and Human Services.

International Search Report and Written Opinion of the International Searching Authority, issued in PCT/US2005/009344, mailed Dec. 21, 2005, U.S. Department of Health and Human Services.

International Preliminary Report on Patentability, date, issued in PCT/US2005/009344, mailed Oct. 5, 2006, U.S. Department of Health and Human Services.

Tamura et al, "Synthesis of Hydrophilic Ultrafine Nanoparticles Coordinated With Carbohydrate Cluster", *Journal of Carbohydrate Chemistry*, vol. 21, No. 5, 2002 (pp. 445-449).

Åkerman et al., "Nanocrystal Targeting in Vivo", PNAS vol. 99 No. 20, Oct. 1, 2002 (pp. 12617-12621).

www.qdots.com/new/technology, Quantum Dot Corporation, Oct. 21, 2003 (15 pages).

Joseph J. Barchi, Jr. & Sergei Svarovsky, "Glycononotechnology: Construction and Properties of Sugar/Peptide-Bearing Nanoparticles", slide presentation Boston, MA, May 5, 2003 (19 pages).

Chan et al., "Luminescent Quantum Dots for Multiplexed Biological Detection and Imaging", *Current Opinion in Biotechnology* 2002, vol. 13, Elsevier Science, Ltd. (pp. 40-46).

Dubertret et al., "In Vivo Imaging of Quantum Dots Encapsulated in Phospholipid Micelles", *Science* vol. 298, Nov. 29, 2002 (pp. 1759-1762).

Larson et al., "Water-Soluble Quantum Dots for Multiphoton Fluorescence Imaging in Vivo", *Science* vol. 300, May 30, 2003 (pp. 1434-1436).

Wang et al., "Stabilization of Inorganic Nanocrystals by Organic Dendrons", *J. Am. Chem. Soc.* vol. 124, No. 10, Feb. 14, 2002 (pp. 2293-2298).

"Dynamics of Human Cells Revealed by Quantum Dots", *Bio-IT World—Best Practices*, Jun. 13, 2005 (pp. 1-2).

Glinsky et al., "The Role of Thomsen-Friedenreich Antigen in Adhesion of Human Breast and Prostate Cancer Cells to the Endothelium", *Cancer Research*, vol. 61, Jun. 15, 2001 (pp. 4851-4857).

Westenhoff, "Quantum Dot on a Rope", *J. Am. Chem. Soc.* vol. 124, No. 11, 2002 (pp. 2448-2449).

Chan, "Quantum Dot Bioconjugates for Ultrasensitive Nonisotopic Detection", *Science*, vol. 281, Sep. 25, 1998 (pp. 2016-2018).

Lawless et al., "Bifunctional Capping of CdS Nanoparticles and Bridging to TiO2" *J. Phys. Chem.*, vol. 99, Jun. 1, 1995 (pp. 10329-10335).

Wu et al., "Immunofluorescent Labeling of Cancer Marker Her2 and Other Cellular Targets with Semiconductor Quantum Dots", *Nature Biotechnology*, vol. 21, Jan. 2003 (pp. 41-46).

Otsuka et al., "PEGylated Nanoparticles for Biological and Pharmaceutical Applications", *Advanced Drug Delivery Reviews*, vol. 55, 2003 (pp. 403-419).

Gao, "In Vivo Cancer Targeting and Imaging With Semiconductor Quantum Dots", *Nature Biotechnology*, vol. 22, No. 8, Aug. 2004 (pp. 969-976)—[published online Jul. 18, 2004].

Pale-Grosdemange et al., "Formation of Self-Assembled Monolayers by Chemisorption of Derivatives of Oligo(ethylene glycol) of Structure $HS(CH_2)_{11}(OCH_2CH_2)_m OH$ on Gold", J. Am. Chem. Soc., vol. 113, 1991 (pp. 12-20).

Aldana et al., "Photochemical Instability of CdSe Nanocrystals Coated by Hydrophilic Thiols", J. Am. Chem. Soc., vol. 123, 2001 (p. 8844-8850).

Barrientos et al., "Gold Glyconanoparticles: Synthetic Polyvalent Ligands Mimicking Glycolcalyx-Like Surfaces as Tools for Glycobiological Studies", Chem. Eur. J., vol. 9, 2003, (p. 1909-1921).

Barchi et al., "Sugar-Coated Nanoparticles: Novel Scaffolds for the Study of Glycan and Glycopeptide-Mediated Processes", International Carbohydrates Symposium, Glasgow, Scotland, Jul. 2004.

Svarovsky et al., "Development of multivalent gold and semiconductor nanoparticles encapsulated with tumor associated glycoantigens as antimetastatic and early cancer detection agents", American Chemical Society National Meeting, Anaheim, California, Mar. 27-Apr. 1, 2004.

Liang et al., "Functionalized CdSe quantum dots as selective silver ion chemodosimeter", Analyst, 129(7), Jul. 2004, pp. 619-622.

Lin et al., "Studies on quantum dots synthesized in aqueous solution for biological labeling via electrostatic interaction", Anal. Biochem., 319(2), pp. 239-243, Aug. 15, 2003.

Chen et al., "Luminescent CdS quantum dots as selective ion probes", published in Anal. Chem., 74(19), Oct. 1, 2002, pp. 5132-5138.

Gaponik et al., "Thiol-Capping of CdTe Nanocrystals: An Alternative to Organometallic Synthetic Routes", J. Phys. Chem. B, vol. 106, No. 29, 2002, (pp. 7177-7185).

Zheng et al., "Ethylene Glycol Monolayer Protected Nanoparticles for Eliminating Nonspecific Binding with Biological Molecules", J. Am. Chem. Soc., vol. 125, No. 26, 2003, (pp. 7790-7791).

Svarovsky et al., "Highly efficient preparation of tumor antigen-containing glycopeptide building blocks from novel pentenyl glycosides", Carbohydrate Research, vol. 338, 2003, (pp. 1925-1935) (published on the internet on Aug. 11, 2003).

Ballou et al., "Noninvasive Imaging of Quantum Dots in Mice", Bioconjugate Chem., vol. 15, No. 1, 2004 (pp. 79-86).

Chan et al., "Nanocrystal biolabels with releasable fluorophores for immunoassays", (In process; Abstract only), Anal. Chem., Jul. 1, 2004, vol. 76, No. 13, pp. 3638-3645.

(Search 1) Results of LEXIS search performed Sep. 2004. Search string = atleast10(quantum dot or quantum confin! or nanocrystal!) and atleast109bio!) and (mercaptoalkanoic or mercaptoalky! or mercaptosuccinic or mercaptoformic or mercaptoacetic or mercaptopropionic or mercaptobutyric or mercaptovaleric or mercaptocaproic or mercaptocaprylic or mercapto***oic or mercapto**oic or thioalkanoic or thioalky! or thiosuccinic or thioformic or thioacetic or thiopropionic or thiobuyric or thiovaleric or thiocaproic or thiocaprylic or thio*oic or thio****oic).

(Search 2) Results of LEXIS search performed Sep. 2004. Search string = atleast5(quantum dot or quantum confin! or nanocrystal!) and atleast5(bio!) and atleast3(glycol).

(Search 3) Results of LEXIS search performed Sep. 2004. Search string = (quantum dot or quantum confin! or nanocrystal!) and bio! and (mercapto! or thio!).

(Search 4) Results of LEXIS search performed Sep. 2004. Search string = quantum dot or quantum confin! or nanocrystal!) and bio! and glycol.

Faulkner, "La. Tech Researches "Smart Tattoo" To Benefit Diabetics", www.thenewsstar.com, Oct. 22, 2003 (pp. 1-2).

Chen, "Synthesis of Glyconanospheres Containing Luminescent CdSe-ZnS Quantum Dots", *Nano Letters*, vol. 3, No. 5, 2003 (pp. 581-584).

* cited by examiner

BIOFUNCTIONALIZED QUANTUM DOTS FOR BIOLOGICAL IMAGING

BACKGROUND OF THE INVENTION

The present invention relates to biofunctionalized quantum dots, which can be used, for example, in biological research, medical research, medical imaging, and medical therapy.

Quantum dots are small semiconductor particles that exhibit quantum confinement. See "Overview," Quantum Dot Corp., (2003) http://www.qdots.com/new/technology/overview.html. A semiconductor has a characteristic band gap, which is the difference in energy between an electron in the valence band and an electron in the conduction band of the semiconductor material. When energy is applied to the material, for example in the form of a photon having a quantum of energy greater than or equal to the band gap, an electron can be stimulated to jump from the valence band to the conduction band. The missing electron in the valence band is referred to as a "hole". See H. B. Gray, "Chemical Bonds," (W. A. Benjamin, Inc., 1973), pp. 208-218. When an electron falls back into a "hole" in the valence band, a photon having a quantum of energy equal to the band gap, and thus a particular wavelength, can be emitted. Thus, materials in which high energy photons can cause electrons to jump into the conduction band, after which electrons can fall back into the valence band, emitting a photon, can exhibit the phenomenon of fluorescence. See A. E. Siegman, "Lasers," University Science Books, 1986), pp. 6-15.

Quantum confinement refers to a phenomenon observed when the physical size of the semiconductor is smaller than the typical radius of the electron-hole pair (Bohr radius). In this case, the wavelength of light emitted through electron-hole recombination is shorter than the wavelength of light emitted by the semiconductor in bulk. The wavelength of light emitted by a semiconductor exhibiting quantum confinement can be termed the characteristic wavelength. Quantum dots can be made to fluoresce at their characteristic wavelength by exposing them to light having a wavelength shorter than the characteristic wavelength. The wavelength of light emitted is dependent on the size of the quantum dot: a smaller size results in a shorter wavelength. Therefore, the characteristic wavelength of a quantum dot can be "tuned" by adjusting the size of the quantum dot. Furthermore, techniques exist for producing quantum dots with narrow monodispersity in size, so that the light emitted from a number of quantum dots has a narrow bandwidth. See "Overview," Quantum Dot Corp., (2003) http://www.qdots.com/new/technology/overview.html.

The essential part of a quantum dot is a nanocrystalline core, a semiconductor in a crystalline state which has a characteristic size of from about 1 to about 100 nm. Quantum dots used for their fluorescing properties can have a size range of from about 1 to about 10 nm. See "Anatomy", Quantum Dot Corp., (2003) http://www.qdots.com/new/technology/dot-tech.html.

The quantum efficiency refers to the ratio of the number of photons emitted to the number of photons to which the quantum dot is exposed and which stimulate light emission.

To increase the quantum efficiency of a nanocrystalline core, and thereby enhance the intensity of fluorescence, the nanocrystalline core can be overcoated with a shell layer of a semiconductor material which has a band gap greater than the band gap of the nanocrystalline core. Bawendi et al, U.S. Pat. No. 6,306,610. A shell layer can also serve to protect the nanocrystalline core from the surrounding environment. If protection of the nanocrystalline core from the environment is important, but enhancement of quantum efficiency is not, a non-semiconductor material can be used for the shell layer. A quantum dot having both a nanocrystalline core and a shell layer can be referred to as a core/shell quantum dot.

Chemical groups, including chemical groups which have an effect on a biological system, can be bound to the surface of a quantum dot. This capacity to be functionalized, together with chemical stability and tunable fluorescing properties, makes quantum dots of great interest in the development of new materials and techniques for biological research and medical diagnosis. Furthermore, quantum dots are much less prone to photobleaching than many conventional dyes.

For most biological or medical applications, in order to be useful, a quantum dot must be rendered hydrophilic and have a biofunctional group attached to its surface. Chan and Nie linked mercaptoacetic acid to cadmium selenide core/zinc sulfide shell quantum dots. They bonded the protein transferrin to the linked mercaptoacetic acid groups by using ethyl-3-(dimethylaminopropyl) carbodiimide. Chan and Nie found that the transferin linked to the quantum dot was recognized by receptors on a cell surface. See Chan and Nie, "Quantum Dot Bioconjugates for Ultrasensitive Nonisotopic Detection", *Science*, v. 281 (1998) p. 2016.

Akerman et al. used cadmium selenide core/zinc sulfide shell quantum dots coated with trioctylphosphine (TOPO), rendered them water soluble, and coated them with mercaptoacetic acid. Thiolated peptides were then linked to the surface of the quantum dots. Akerman et al. also made quantum dots in which thiolated polyethylene glycol and thiolated peptides were linked to mercaptoacetic acid coated quantum dots. They found that the peptide-functionalized quantum dots coupled with corresponding peptide receptors expressed by cells. See Akerman et al., "Nanocrystal targeting in vivo", *Proc. National Academy of Sciences*, v. 99(2) (2002) p. 12617.

Larson et al. encapsulated a cadmium selenide core/zinc sulfide shell quantum dot within a amphiphilic polymer to render the quantum dot hydrophilic. They were able to image fluorescing quantum dots through the skin. Larson et al. suggested that the cadmium selenide core/zinc sulfide shell quantum dots leave the body before breakdown because there were no noticed toxic effects from the cadmium on mice into which they were injected. See Larson et al., "Water-Soluble Quantum Dots for Multiphoton Fluorescence Imaging in Vivo", Science, v. 300 (2003) p. 1434.

Semiconductor nanocrystals can attach trioctylphosphine oxide (TOPO) as a ligand, rendering the semiconductor nanocrystals soluble in organic solvents such as chloroform and toluene, but not soluble in polar solvents such as water and ethanol. In an approach, a cadmium selenide core/zinc sulfide shell quantum dot was first coordinated with TOPO. Molecules in which mannose groups were covalently bonded to a phosphine oxide were then used to replace the TOPO groups on the cadmium selenide core/zinc sulfide shell, rendering the quantum dot hydrophilic. See Tamura et al., "Synthesis of Hydrophilic Ultrafine Nanoparticles Coordinated with Carbohydrate Cluster", *J. Carbohydrate Chemistry*, v. 21(5) (2002) p. 445. However, it is doubtful whether the functionalized quantum dots produced were stable. In another approach, cadmium selenide core/zinc sulfide shell structures coordinated with TOPO were treated with a silathiane and mercaptosuccinic acid. The quantum dots were treated with a solutions of carboxymethyl dextran and of polylysine and treated with 1-ethyl-3-(3)-dimethylaminopropyl carbodiimide, which acts as a crosslinking agent. See Chen et al., "Synthesis of Glyconanospheres Containing Luminescent CdSe—ZnS Quantum Dots", *Nano Letters*, v. 3(5) (2003) p581.

The applicants attempted to displace a TOPO layer on a cadmium selenide core/zinc sulfide shell quantum dot commercially available from Evident Technologies with a hydrophilic thiol compound using the modified phase-transfer procedure developed by Wang et al. See Wang et al., *J. Am. Chem. Soc.*, v. 106 (2002) p. 2293. However, either the displacement was incomplete or the resultant functionalized quantum dots were fragile and did not survive mild ultrafiltration or dialysis and precipitated or flocculated shortly after the hydrophilic thiol compound was removed from the solution.

Bawendi et al. functionalized quantum dots with proteins and with oligonucleotides. The procedure used started with TOPO-capped cadmium selenide core/zinc sulfide shell quantum dots with which the proteins or oligonucleotides were linked. Bawendi et al., U.S. Pat. No. 6,306,610.

Gaponik et al. synthesized hydrophilic cadmium telluride core/cadmium sulfide shell quantum dots using an aqueous synthesis approach. In the approach, a cadmium salt and a mercapto-compound were mixed in an aqueous solution through which hydrogen telluride was bubbled. Cadmium telluride nanocrystals were formed which were capped at the surface with the mercapto compound. The mercapto-compound was linked to the cadmium telluride core through the sulfur atom. Thus, the cadmium telluride core was understood to be surrounded by a layer of sulfur atoms, which also were present deeper in the core, and which bonded to the cadmium atoms to form a cadmium sulfide shell layer. The hydrophilic cadmium telluride core/cadmium sulfide shell quantum dots exhibited good photostability; i.e., fluoresced over a long duration of illumination. Gaponik et al., "Thiol-Capping of CdTe Nanocrystals: An alternative to Organometallic Synthetic Routes", *J. Phys. Chem.* B, v. 106 (2002) p. 7177.

For a preparation of quantum dots with biofunctional groups linked to their surfaces to be useful in biological research, medical diagnostic, and medical therapeutic applications, the quantum dots must fluoresce brightly, be hydrophilic, and be stable in water not containing excess biofunctional groups for prolonged periods of time.

Coupling of receptors to cell-surface saccharides mediates many relevant biological processes, including differentiation, motility, adhesion, tumor progression, and metastasis. Therefore, quantum dots functionalized with saccharides are of interest for biological research, medical diagnostic, and medical therapeutic applications. However, quantum dots suitable for such applications have up until now not been developed.

There thus remains a need for quantum dots which fluoresce brightly, have biofunctional groups linked to their surfaces, are hydrophilic, and are stable in aqueous solution. There is also a continuing need for quantum dots which have saccharides linked to their surfaces.

SUMMARY OF THE INVENTION

It is therefore an object of the present invention to provide novel biofunctionalized quantum dots which fluoresce brightly, are hydrophilic, and are stable in aqueous solution. It is further an object of the present invention to provide quantum dots which have saccharides linked to their surfaces.

An embodiment of a biofunctionalized quantum dot according to the invention includes a nanocrystalline core exhibiting quantum confinement and having a band gap and a surface, a mercaptoalkanoic acid linked to the surface, and a biofunctional group linked to the surface. The ratio of mercaptoalkanoic acid molecules to biofunctional group molecules linked to the surface can be in the range of from about 1:1 to about 5:1. The mercaptoalkanoic acid can be chosen from a set of mercaptoalkanoic acids not including mercaptosuccinic acid. The mercaptoalkanoic acid can be chosen to have only one carboxyl group and comprising less than seven carbon atoms. The mercaptoalkanoic acid can be mercaptoacetic acid.

In an embodiment, the biofunctional group is chosen to have a molecular weight greater than a molecular weight of the mercaptoalkanoic acid. The biofunctional group can be chosen to have a molecular volume greater than a molecular volume of the mercaptoalkanoic acid.

In another embodiment of a biofunctionalized quantum dot according to the invention, a shell layer overcoats a nanocrystalline core. The shell layer can include cadmium sulfide and the nanocrystalline core can include cadmium telluride, cadmium selenide, mercury telluride, and mercury selenide.

The biofunctional group on a quantum dot according to the invention can be a saccharide. For example, the saccharide can be a tumor-associated carbohydrate antigen. The saccharide can be Thomsen-Friedenreich disaccharide. The biofunctional group on a quantum dot according to the invention can be chosen from a set of saccharides not comprising mannose or dextran. The saccharide can be directly linked to a sulfur atom, the sulfur atom being linked to the surface of the nanocrystalline core. The saccharide can be linked to a linking group, the linking group linked to a sulfur atom, and the sulfur atom linked to the surface of the nanocrystalline core. The linking group can include a carbon atom.

In another embodiment, the biofunctionalized quantum dot is stable in aqueous solution under storage in the dark at 4° C. for at least 4 months with respect to luminescence, precipitation, flocculation, and leaching of the biofunctional group.

In an embodiment, a formulation includes a liquid, a biofunctionalized quantum dot, a mercaptoalkanoic acid linked to the surface of the nanocrystalline core of the quantum dot, and a biofunctional group linked to the surface and the biofunctionalized quantum dot is dissolved or suspended in the liquid and does not precipitate or flocculate.

In an embodiment, a biofunctionalized quantum dot is made by refluxing a biofunctional group-thiol of Formula III with a cadmium salt, hydrogen-alkali-telluride or hydrogen-alkali-selenide, and a suitable solvent to produce a quantum dot in a solution. The $R_1$ group includes at least one carbon atom. Suitable solvents include water and N,N-dimethylformamide (DMF). The refluxing can be conducted in a range of from about 24 to about 48 hours. The refluxed mixture can further include a mercaptoalkanoic acid, for example, mercaptoacetic acid. The biofunctional group can be a saccharide, for example, Thomsen-Friedenreich disaccharide. The refluxing can be carried out with Thomsen-Friedenreich disaccharide and mercaptoacetic acid in a molar ratio of from about 1:1 to about 5:1. After refluxing, the solution can be purified and dried to obtain a biofunctionalized quantum dot preparation. The purifying can include separating the biofunctionalized quantum dot from the remainder of the solution by filtration through an ultrafiltration membrane with a cutoff of about 50 kilodaltons. The purified and dried biofunctionalized quantum dot preparation can be dissolved or suspended in an aqueous solvent.

A biofunctional group-thiol of Formula III can be made by reacting a glycoside of Formula I with an alkylthio acid in the presence of a catalyst to produce a thioester of Formula II, debenzylidenating the thioester of Formula II, and hydrolyzing the thioester of Formula II to produce the biofunctional group-thiol of Formula III; the group $R_2$ includes at least one carbon atom.

In an embodiment, a biofunctionalized quantum dot is made as follows. A glycoside of Formula IV is reacted with an alkylthio acid in the presence of 2,2'-azobisisobutyronitrile in 1,4-dioxane at about 75° C. to produce a thioester of Formula V, debenzylidinating the thioester of Formula V. The thioester of Formula V is debenzylidinated and the debenzylidinated thioester of Formula V is hydrolyzed to produce a Thomsen-Friedenreich-thiol of Formula VI. The Thomsen-Friedenreich-thiol of Formula VI is refluxed with cadmium perchlorate, mercaptoacetic acid, hydrogen sodium telluride, and a suitable solvent, either water or N,N-dimethylformamide, to produce a Thomsen-Friedenreich-functionalized quantum dot in a solution.

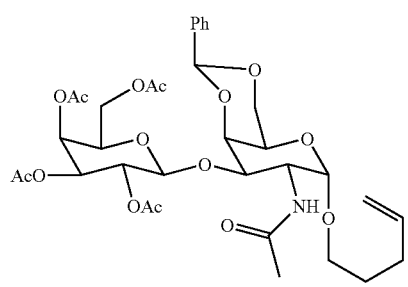

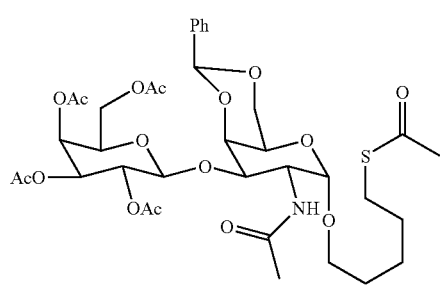

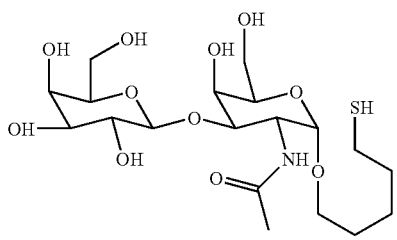

The debenzylidination step can include treating the thioester of Formula V with aqueous acetic acid at about 60° C. and evaporating to obtain the debenzylidinated thioester. Alteratively, the debenzylidination step can include treating the thioester of Formula V with acetyl chloride in methanol, adding pyridine to the thioester of Formula V with acetyl chloride in methanol for quenching the reaction, and evaporating to obtain debenzylidinated thioester. The hydrolyzing step can include treating the debenzylidinated thioester with sodium methoxide in methanol to produce the Thomsen-Friedenreich-thiol of Formula VI. Alternatively, the hydrolyzing step can include treating the debenzylidinated thioester with sodium methoxide in methanol while bubbling air through the debenzylidinated thioester, sodium methoxide, and methanol to produce a Thomsen-Friedenreich-disulfide of Formula VII and treating the Thomsen-Friedenreich-disulfide of Formula VII with dithiothreitol in water to produce the Thomsen-Friedenreich-thiol of Formula VI.

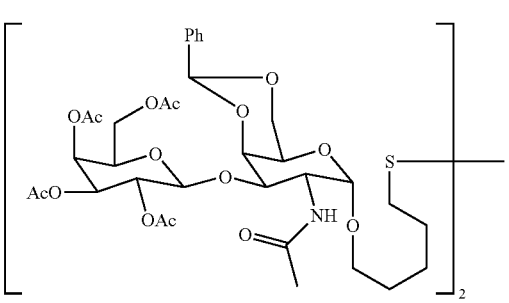

In an embodiment, a biofunctionalized quantum dot is used for imaging. The biofunctionalized quantum dot, of which the biofunctional group includes a saccharide, or which includes a mercaptoalkanoic acid linked to the nanocrystalline surface, is contacted with a biological material. The biological material is exposed to light having a wavelength effective to cause the quantum dot to fluoresce and the fluorescing quantum dots are imaged. The biofunctional group can be Thomsen-Friedenreich disaccharide. The biological material can include a cell culture or can include a tissue. The biofunctionalized quantum dot can be dissolved or suspended in a biocompatible aqueous solvent. Contacting the biofunctionalized quantum dot with biological material can included injecting the biofunctionalized quantum dot into tissues of a living animal.

The fluorescing quantum dot adhered to secretions of the biological material can be imaged. Tissue which imaging identifies as tissue to which the biofunctional group exhibits high affinity can be identified as tissue in a diseased or abnormal state, for example, a cancerous state.

In an embodiment, several types of biofunctionalized quantum dots are used for imaging. The biofunctional groups of the biofunctionalized quantum dots include a saccharide, or the biofunctionalized quantum dots include a mercaptoalkanoic acid linked to the nanocrystalline surface. Each type of biofunctionalized quantum dot has a characteristic wavelength distinct from the other types. Each type of quantum dot is functionalized with a different antigen or a different set of antigens. The several types of biofunctionalized quantum dots are contacted with a biological material, the biological material is exposed to light having a wavelength effective to cause the quantum dots to fluoresce, and the fluorescing quantum dots are imaged.

In an embodiment, a biofunctionalized quantum dot is used for therapy. The biofunctional group of the biofunctionalized quantum dot includes a saccharide, or the biofunctionalized quantum dot includes a mercaptoalkanoic acid linked to the nanocrystalline surface. The biofunctionalized quantum dot is contacted with a biological material and thereby treats a disease. The biofunctional group can be an immune-response-stimulating group. The biofunctional group can be a tumor-associated antigen. The biofunctional group can be Thomsen-Friedenreich disaccharide. The contacting with a biological material can include injecting the biofunctionalized quantum dot into tissues of a living animal in order to treat cancer.

A biofunctionalized quantum dot used for therapy can have a therapeutic agent linked to the surface. The shell layer or the nanocrystalline shell of a biofunctionalized quantum dot used for therapy can include a therapeutic agent.

In an embodiment, a biofunctionalized quantum dot is used to coat a device which, when not coated, is in contact with a biological material. The biofunctional group of the biofunctionalized quantum dot includes a saccharide, or the biofunctionalized quantum dot includes a mercaptoalkanoic acid linked to the nanocrystalline surface.

In an embodiment, a cell-quantum dot complex includes a biofunctionalized quantum dot linked to a cell. The biofunctional group of the biofunctionalized quantum dot includes a saccharide, or the biofunctionalized quantum dot includes a mercaptoalkanoic acid linked to the nanocrystalline surface. The biofunctional group can be Thomsen-Friedenreich disaccharide.

DETAILED DESCRIPTION

Figure 1:
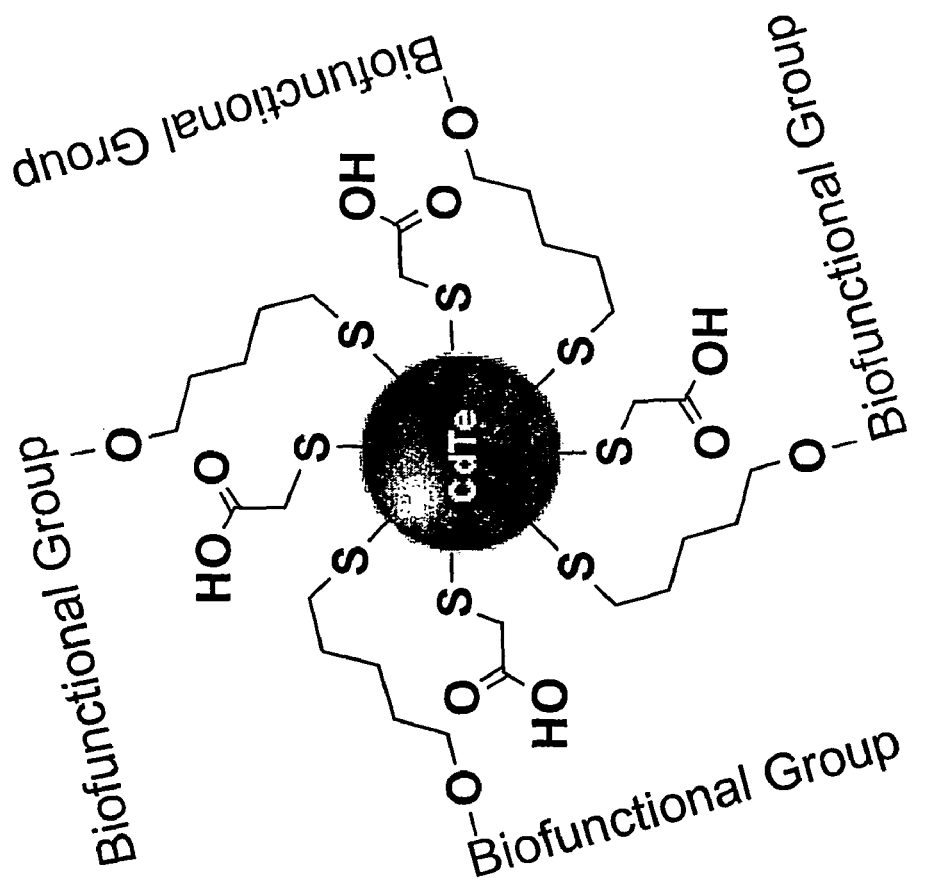
FIG. 1 is a schematic of cadmium telluride nanocrystal functionalized with mercaptoacetic acid and with a biofunctional group-thiol.

Embodiments of the invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without parting from the spirit and scope of the invention. All references cited herein are incorporated by reference as if each had been individually incorporated.

In an embodiment of a biofunctionalized quantum dot, a biofunctional group is linked to the surface of a nanocrystalline core exhibiting quantum confinement. Examples of core materials included in the nanocrystalline core include zinc sulfide, zinc selenide, zinc telluride, cadmium sulfide, cadmium selenide, cadmium telluride, mercury sulfide, mercury selenide, mercury telluride, magnesium telluride, aluminum phosphide, aluminum arsenide, aluminum antimonide, gallium nitride, gallium phosphide, gallium arsenide, gallium antimonide, indium nitride, indium phosphide, indium arsenide, indium antimonide, aluminum sulfide, lead sulfide, lead selenide, germanium, or silicon. Core materials also include other group II—group VI compounds, group III—group V compounds, and group IV compounds. Core materials also include other semiconductor materials. The core material may also be formed of an alloy, compound, or mixture of these compounds and elements which are suitable core materials. For example, the core material can be a mercury-cadmium sulfide compound. The core material can also be doped with one or more suitable dopants.

In an embodiment, a biofunctionalized quantum dot includes a shell layer overcoating and surrounding a nanocrystalline core. The shell layer can include a single layer of a shell material different from the core material which forms the nanocrystalline core. The shell layer can include a semiconductor material with a band gap greater than the band gap of the nanocrystalline core. Examples of shell materials included in the shell layer include zinc oxide, zinc sulfide, zinc selenide, zinc telluride, cadmium oxide, cadmium sulfide, cadmium selenide, cadmium telluride, mercury oxide, mercury sulfide, mercury selenide, mercury telluride, magnesium telluride, aluminum nitride, aluminum phosphide, aluminum arsenide, aluminum antimonide, gallium nitride, gallium phosphide, gallium arsenide, gallium antimonide, indium nitride, indium phosphide, indium arsenide, indium antimonide, aluminum sulfide, lead sulfide, lead selenide, germanium, or silicon. Shell materials also include other group II—group VI compounds, group II—group V compounds, and group IV compounds. Shell materials also include other semiconductor materials. The shell material may also be formed of an alloy, compound, or mixture of these compounds and elements which are suitable shell materials. The term quantum dot may refer to a nanocrystalline core without a shell layer, or a to the composite structure of a nanocrystalline core with a shell layer. The core material can also be doped with one or more suitable dopants.

A shell layer can include a single layer of the atoms which form the shell material. For example, a cadmium selenide or cadmium telluride nanocrystalline core can be overcoated with a cadmium sulfide shell. The cadmium sulfide shell can be formed of sulfur atoms bonded to cadmium atoms on the surface of or within the cadmium selenide or cadmium telluride nanocrystalline core. As another example, a mercury selenide or mercury telluride nanocrystalline core can be overcoated with a mercury sulfide shell. The mercury sulfide shell can be formed of sulfur atoms bonded to mercury atoms on the surface of or within the mercury selenide or mercury telluride nanocrystalline core.

A quantum dot is biofunctionalized when the quantum dot has molecules, referred to as biofunctional groups, linked to its surface which act to change the response of a biological system from that resulting from contact with a non-functionalized nanocrystalline core or shell. The term "link" refers to an attractive association of an atom or molecule with another atom or molecule, for example, a covalent bond, an ionic bond, a hydrogen bond, or a bond or interaction of another type. As an example, biofunctional groups may be attached to the surface of a nanocrystalline core or a shell which stimulate an immunological response, allow the quantum dot as a whole to adhere to biological material or secretions of the biological material, e.g., antibodies, and render the quantum dot as a whole biologically inert so that the biological system does not "see" the quantum dot and does not respond. A biofunctional group which stimulates an immunological response can be referred to as an immune-response-stimulating group.

In another embodiment, a biofunctional group is linked to the surface of a nanocrystalline core and a mercaptoalkanoic acid is linked to the surface of the nanocrystalline core. In an embodiment, the mercaptoalkanoic acid has one mercapto group, one carboxyl group and from one to six carbon atoms. For example, the mercaptoalkanoic acid can be mercaptoacetic acid.

The biofunctional group can be directly linked to the nanocrystalline core, or it can be linked to a shell layer which overcoats the nanocrystalline core. Certain saccharides are biofunctional groups. In this application, the term "saccharide" refers to mono-, di-, tri-, and oligosaccharides. The saccharide can be a saccharide found in nature, or can be a saccharide which is not found in nature. A saccharide may be, for example, an antigen found on the membrane of a tumor cell or a bacterium. For example, Thomsen-Friedenreich disaccharide is found on the surface of many human cancer cells but not on the surface of normal human cells. A saccharide found on the surface of cancer cells, but not on the surface of normal human cells can be referred to as a tumor-associated carbohydrate antigen.

A biofunctional group can be directly linked to a nanocrystalline core or a shell layer. A biofunctional group can also be linked to an atom which has high affinity for or integrates with a nanocrystalline core or a shell layer so that the biofunctional group is linked through the atom to the nanocrystalline core or shell layer. A biofunctional group can also be linked to a "linking group", which is in turn linked to the nanocrystalline core or the shell layer. A linking group may play a number of roles. For example, a linking group may act as a "spacer" between the nanocrystalline core or shell layer and the biofunctional group so that the biofunctional group can assume a conformation required to stimulate or suppress the response of a biological system as desired. A linking group can also act to separate charge in or on the nanocrystalline core or shell layer from the biofunctional group. A linking group can facilitate a method of linking a biofunctional group to a nanocrystalline core or shell layer. A biofunctional group can be linked to a linking group, the linking group in turn linked to an atom which has a high affinity for and thus links to the nanocrystalline core or shell layer or which integrates with the nanocrystalline core or shell layer. For example, a biofunctional group can be linked to a sulfur atom and the sulfur atom in turn linked to the surface of a nanocrystalline core. As another example, a saccharide which is a biofunctional group can be linked to a linking group comprising a chain of at least one carbon atom. The linking group can in turn be linked to a sulfur atom. The sulfur atom can then be linked to a nanocrystalline core, for example, a cadmium selenide or cadmium telluride nanocrystalline core. In an embodiment, a Thomsen-Friedenreich disaccharide is covalently bonded to a chain of five carbon atoms, which is in turn bonded to a sulfur atom, which is in turn bonded to a nanocrystalline core of cadmium telluride or cadmium selenide.

In an embodiment, a quantum dot is functionalized with a biofunctional group and with a mercaptoalkanoic acid. The biofunctional group and the mercaptoalkanoic acid are selected so that the biofunctional group has a molecular weight greater than the molecular weight of the mercaptoalkanoic acid. Alternatively, the biofunctional group and the mercaptoalkanoic acid are selected so that the biofunctional group has a molecular volume greater than the molecular volume of the mercaptoalkanoic acid. Such a selection of the biofunctional group and the mercaptoalkanoic acid can be made to ensure that the mercaptoalkanoic acid groups on the surface of the quantum dot do not shield or screen the biofunctional groups from the environment, for example, from molecules or structures in a biological material, such as in a living animal.

An embodiment of a method for making a biofunctionalized quantum dot is now described. A biofunctional group-thiol of Formula III, in which $R_1$ represents a group containing one or more carbon atoms, can be refluxed with a cadmium salt, e.g., cadmium perchlorate, a hydrogen alkali telluride, e.g., hydrogen sodium telluride, and a suitable solvent, e.g., water or N,N-dimethylformamide, to produce a quantum dot in which the biofunctional group-thiol of Formula III is linked to the surface of a nanocrystal of cadmium telluride. A hydrogen alkali selenide, e.g., hydrogen alkali selenide, can be used instead of a hydrogen alkali telluride to produce a quantum dot in which the biofunctional group-thiol is linked to the surface of a nanocrystal of cadmium selenide. In an embodiment, the biofunctional group-thiol of Formula III can be a Thomsen-Friedenreich-thiol. In general, the longer refluxing is conducted, the larger the biofunctionalized quantum dots produced will be. In an embodiment, refluxing is conducted for a duration of from about 24 hours to about 48 hours. For example, refluxing can be conducted for 39 hours.

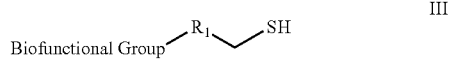

In another embodiment, the mixture which is refluxed also contains a mercaptoalkanoic acid, e.g., mercaptoacetic acid. A biofunctionalized quantum dot is thereby formed in which the biofunctional group-thiol and a mercaptoalkanoic acid group are linked to the surface of a nanocrystal of cadmium telluride when a hydrogen alkali telluride is used, as shown in FIG. 1. The biofunctional group-thiol and a mercaptoalkanoic acid group can also be linked to the surface of a nanocrystal of cadmium selenide when a hydrogen alkali selenide is used. In an embodiment, the biofunctional group is Thomsen-Friedenreich disaccharide, the mercaptoalkanoic acid is mercaptoacetic acid, and the Thomsen-Friedenreich-thiol and the mercaptoacetic acid are present in a molar ratio of from about 1:1 to about 5:1 in the mixture. For example, they can be in a molar ratio of about 3.4:1.

In an embodiment, the biofunctional group-thiol of Formula III can be formed by reacting a glycoside of Formula I with a alkylthio acid in the presence of a catalyst to produce a thioester of Formula II, in which $R_2$ represents a group containing one or more carbon atoms. The thioester of Formula II can then be debenzylidinated and hydrolyzed to produce the biofunctional group-thiol of Formula III in solution.

In an embodiment, the glycoside can be selected to produce a Thomsen-Friedenreich-thiol for the compound of Formula III.

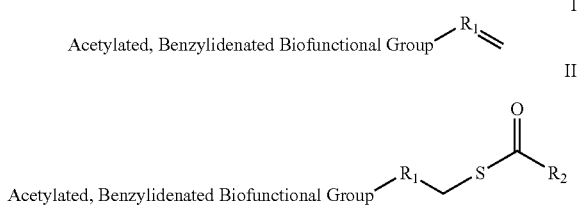

In an embodiment, the solution containing biofunctionalized quantum dots illustrated in FIG. 1 can be purified, and the purified solution can be dried to isolate a preparation of biofunctional group-functionalized quantum dots. For example, the solution can be filtered through a membrane with a cutoff in the range of 10 to 100 kilodaltons. The cutoff can be selected so that only the desired quantum dots less than a certain size pass through and larger quantum dots and particles are retained; in this case the permeate passing through the filter is dried to obtain isolated biofunctionalized quantum dots. Alternatively, the cutoff can be selected so that the desired quantum dots of greater than a certain size are retained and smaller quantum dots and particles pass through; in this case the retentate retained by the filter is dried to isolate biofunctionalized quantum dots. The solution containing the quantum dots can also be forced through a filter with a larger cutoff, the permeate then passed through a filter with a smaller cutoff, and the retentate of the filter with the smaller cutoff then dried to isolate biofunctionalized quantum dots. Membranes of various types can be used, for example, an ultrafiltration membrane can be used or a dialysis membrane can be used. As an example, the solution containing the quantum dots can be passed through an ultrafiltration membrane with a cutoff of about 50 kilodaltons and the retentate dried to isolate biofunctionalized quantum dots. The isolated biofunctionalized quantum dots can be redissolved or resuspended in an aqueous solvent, for example, a biocompatible aqueous solvent, for further use. A biocompatible aqueous solvent could be a solvent containing components in addition to water and the quantum dots which improve the performance of the water-dissolved or water-suspended quantum dots when they are applied to a biomaterial. For example, a biocompatible aqueous solvent may be adjusted to have similar salinity and pH as a tissue into which it is to be injected.

In an embodiment, a biofunctionalized quantum dot is linked to a cell to form a cell-quantum dot complex. For example, the biofunctional group on the quantum dot may act as a ligand which couples with a receptor on the surface of a cell. The biofunctional group on the quantum dot can be, for example, a saccharide, such as Thomsen-Friedenreich disaccharide. For example, the Thomsen-Friedenreich disaccharide may act as a ligand which couples with a receptor protein, galectin-3, on an endothelial cell. In addition to a biofunctional group, the quantum dot may have other groups on its surface, such as a mercaptoalkanoic acid, e.g., mercaptoacetic acid.

In an embodiment, the biofunctionalized quantum dots are in the form of a formulation. Such a formulation includes a liquid and biofunctionalized quantum dots dissolved or suspended in the liquid so that the solution or suspension does not precipitate or flocculate. The biofunctionalized quantum dots according to the invention, when mixed with water, form a solution which is clear, although it may be colored. Thus it appears that the quantum dots dissolve in water. However, the literature on hydrophilic quantum dots often refers to a suspension of quantum dots, it may be that although when mixed with water, the resultant composition is clear, the term "suspension" is used because of the greater size of quantum dots with respect to low molecular weight molecules.

In an embodiment, the biofunctionalized quantum dots in a formulation have a mercaptoalkanoic acid, e.g., mercaptoacetic acid, linked to their surfaces. The biofunctional group can be a saccharide, for example, Thomsen-Friedenreich disaccharide.

Biofunctionalized quantum dots can be used in systems for assessing characteristics of a biological material. For example, biofunctionalized quantum dots can be used to diagnose disease states of tissue. Such tissue could be evaluated in vivo, i.e., while still in an organism, or in vitro, e.g., a biopsy sample could be evaluated. A biological material may either be living, i.e., exhibiting metabolism, or nonliving. A non-exhaustive list of examples of biological materials include isolated cells, a number of cells which do not act cooperatively, cells in a cell culture, cells in or removed from a multicellular organism, e.g., an animal, tissue in or removed from a multicellular organism, e.g., portions of organs such as liver, structures in or removed from an organism, e.g., hair, contents of cells, and material secreted by cells or by an organism, e.g., serum, mucus, proteins, or antibodies.

Biofunctionalized quantum dots can be used in biological or medical imaging applications. In an embodiment, a biofunctionalized quantum dot is contacted with a biological material. The biofunctionalized quantum dots and biological material are then exposed to light having a wavelength effective to cause the quantum dot to fluoresce, i.e., light with a wavelength shorter than the characteristic wavelength of the quantum dot. The biofunctionalized quantum dots and biological material can then be imaged, e.g., through chemical photography or a video camera. The fluorescing regions of the biological material are regions to which the biofunctional groups on the quantum dots adhere. By noting differences in fluorescence intensity resulting from different number density of quantum dots in different regions of the biological material, differences in characteristics of these regions may be detected. Such differences in characteristics can be used to identify tissue in a diseased or abnormal state, for example, cancerous tissue or tissue infected by bacteria, parasites, or viruses.

Scientists from the University of Missouri have shown that cancer-associated carbohydrate T antigen, e.g., Thomsen-Friedenreich disaccharide, plays a leading role in docking breast and prostate cancer cells onto endothelium by specifically interacting with an endothelium-expressed protein, galectin-3. The presence of cancer cells in the body may stimulate expression of galectin-3 in endothelial cells.

Biofunctionalized quantum dots according to the invention can be injected into an organism, for example, into the tissues, including the circulatory system, of a living animal. For example, the biofunctionalized quantum dots can be dissolved or suspended in a biocompatible aqueous solvent, and the solution or suspension then injected into the body. The Thomsen-Friedenreich-functionalized quantum dots of the invention would adhere to cells which express galectin-3, in particular, endothelial cells which have been stimulated to express large amounts of galectin-3. The body or a biopsy of tissue from the body can then be exposed to light which causes the quantum dots to fluoresce, the body or biopsy sample can then be imaged. By noting which regions of tissue fluoresce most intensely, the state of advancement of a tumor, for example, a metastasizing tumor, can be determined. See Glinsky et al., "The role of Thomsen-Friedenreich antigen in adhesion of human breast and prostate cancer cells to the endothelium", Cancer Res., 61 (12): 4851-4857, Jun. 15, 2001. The fact that the biofunctionalized quantum dots of the present application are water-soluble and biocompatible makes them particularly advantageous for use in evaluating tissue in vivo or in vitro.

Quantum dots can be functionalized with biological receptors which couple with antigens on cancer cells, these antigens either not being present in normal cells or being present on cancer cells in much greater concentration than in normal cells. Similarly, quantum dots can be functionalized with antigens which couple with receptors on cancer cells, these receptors either not being present in normal cells or being present on cancer cells in much greater concentration than in normal cells. By contacting the quantum dots with tissue in the body or in an in vitro sample and imaging, regions of tissue in which cancer cells have proliferated can be detected.

In an embodiment, biofunctionalized quantum dots of the invention are used in a biological or medical analysis system. For example, a quantum dot can be functionalized with an antigen to which a pathogen sought to be detected has affinity, e.g., through a receptor on the pathogen. A biological material or substance secreted from a biological material can be brought into contact with the biofunctionalized quantum dot. Coupling of a pathogen to the quantum dot can be detected, for example, by passing a fluid containing the quantum dots and pathogens over an assay plate on which the antigen is fixed. A pathogen to which a quantum dot is coupled and having affinity to an antigen will then couple to the antigen fixed to the plate. By shining light of a shorter wavelength than the characteristic wavelength of the quantum dot, any quantum dots in a pathogen-quantum dot complex affixed to the plate is made to fluoresce. Such fluorescence is then indicative of the presence of the pathogen.

Similarly, different types of quantum dots can be produced, each functionalized with a different antigen corresponding to an antigen fixed to a specific region of an assay plate. The quantum dots can then be combined with the sample suspected of containing pathogens. A fluid containing the sample and the quantum dots is then passed over the assay plate. A pathogen bearing a receptor will couple to a quantum dot having the corresponding antigen and to the region of the assay plate having the corresponding antigen. When the quantum dots are made to fluoresce, the fluorescing regions on the plate can be noted. Because the antigen corresponding to a region of the plate is known, the presence of a number of pathogens bearing receptors specific to antigens can be identified.

As another example, the quantum dots can be functionalized with several antigens. In an embodiment, a number of types of quantum dots are made, each type having a specific size and being made of a specific material so that each type fluoresces at a different wavelength. Each type can be functionalized with a different antigen or with a different set of antigens. The antigens present on the quantum dots can then be distributed over and fixed to an assay plate. Pathogens binding to antigens on the quantum dots would then couple to antigens on the plate surface. By shining light of a shorter wavelength than the characteristic wavelengths of the quantum dots, the quantum dots are made to fluoresce. By determining the wavelengths of the light emitted from the quantum dot—pathogen complexes coupled to the plate surface, the presence of pathogens bearing receptors specific to antigens can be identified. Such assay plates can be in a microchip format to form a "lab on a chip" used in small analytical devices or even implanted in the body.

Biofunctionalized quantum dots of the invention can also be used together with an assay plate as follows. An antibody is fixed to an assay plate. A sample which may contain antigens or pathogens bearing antigens is brought into contact with the assay plate. Quantum dots are functionalized with the same antibody and brought into contact with the assay plate. Light of a shorter wavelength than the characteristic wavelength of the quantum dots is then shown on the assay plate. Fluorescence from the quantum dots indicates the presence of the antigen or the pathogen-bearing antigen. This method can be extended to assay plates on which more than one type of antibody is fixed, each antibody being fixed to a specific region of the assay plate. The method can also be extended to a method in which several types of quantum dots fluorescing at different frequencies are functionalized, each type with a different antibody or set of antibodies, the different antibodies are distributed over and fixed to an assay plate, a sample which may contain antigens or pathogen-bearing antigens is brought into contact with the assay plate, and the antibody-functionalized quantum dots are brought into contact with the assay plate.

Biofunctionalized quantum dots can be used in therapeutic applications. For example, cancer cells may express antigens which couple with receptors on normal cells. Such coupling can play a role in metastasis of cancer cells or other interactions of cancer cells with the body. In an embodiment, quantum dots are functionalized with the same antigens which the cancer cells express, the quantum dots may bind to receptors on normal cells and thereby block adhesion of cancer cells to the normal cells. For example, as discussed above, cancer-associated carbohydrate T antigen, e.g., Thomsen-Friedenreich disaccharide, plays a leading role in docking breast and prostate cancer cells onto endothelium by specifically interacting with an endothelium-expressed protein, galectin-3. Thomsen-Friedenreich-functionalized quantum dots could be injected into the body to adhere to endothelial cells which express galectin-3, in particular, endothelial cells which have been stimulated to express large amounts of galectin-3, and thereby block adhesion of the cancer cells to the endothelium. Such therapy could delay or prevent the metastasis of cancer cells. See Glinsky et al., "The role of Thomsen-Friedenreich antigen in adhesion of human breast and prostate cancer cells to the endothelium", Cancer Res., 61 (12): 4851-4857, Jun. 15, 2001.

It is thought that multiple presentations of antigenic saccharides to receptor proteins, i.e., a high concentration of antigenic saccharides, may dramatically increase the strength of coupling between the particle or cell with the antigenic saccharides and the particle or cell with the receptor proteins; this is known as the cluster glycoside effect. Thus, quantum dots can advantageously be used as vehicles to provide antigenic saccharides to receptors proteins, because the antigenic saccharides are present in high concentrations on the surface of the quantum dots.

The biofunctionalized quantum dots presented in this application can be especially useful in that they can be used simultaneously for therapy and diagnosis. For example, biofunctionalized quantum dots can be injected into the body for therapy, and then induced to fluoresce and imaged to monitor the response of the body, especially of diseased tissue, to the therapy.

As discussed above, quantum dots functionalized with an antigen can bind with diseased cells, e.g., cancer cells, which express a receptor for the antigen, and quantum dots functionalized with a receptor can bind with diseased cells, e.g., cancer cells, which express an antigen which couples with the receptor. In an embodiment, the quantum dot, in addition to the biofunctional antigen or receptor, has a therapeutic agent linked to it. By injecting such a quantum dot, site-specific drug delivery can be achieved. Such site-specific therapeutic agent delivery is of great interest in cancer therapy, as the therapeutic agents used can be toxic to normal as well as cancerous cells. The therapeutic agent delivered can be a drug, e.g., a drug to stimulate an immune response, a chemotherapeutic agent, e.g., for killing or weakening a cancer cell, or a radiotherapeutic agent for killing or weakening a cancer cell. Alternatively, the nanocrystalline core or the shell layer of the quantum dot may itself serve as the therapeutic agent. For example, radioisotopes may be used as elements in the formation of the semiconductor nanocrystalline core or of the shell layer. Non-radioactive elements or compounds may be selected for their toxicity to cancer cells and selected so that the semiconductor nanocrystalline core or the shell layer which they form degrades over time, exposing the cancer cells to which the quantum dot is bound to these toxic elements or compounds. Drug-functionalized, radioactive, or chemotoxic quantum dots functionalized with an antigen can also be used to selectively weaken or destroy cells in the body which cancer cells co-opt for their growth or proliferation.

In an embodiment, biofunctionalized quantum dots are used as a component of an immunogenic composition. Tumor-associated antigens expressed by cancerous cells, for example, antigenic saccharides such as Thomsen-Friedenreich disaccharide, can be used to functionalize quantum dots. Introduction of tumor-associated-antigens alone usually fails to stimulate an immune response because of immune self-tolerance. However, multiple and dense presentation of tumor-associated-antigens on the surface of a quantum dot may be recognized by the immune system as distinctly unnatural so that an immune response is stimulated. When injected into the body, these tumor-associated antigen-functionalized quantum dots may stimulate an immune response and thus spur the immune system in attacking the cancerous cells.

In an embodiment, biofunctionalized quantum dots are used to coat surfaces of devices which come into contact with biological material. Examples of such devices are implants or extracorporeal devices, e.g., dialysis machines. For example, the biofunctional groups on the quantum dots can be selected so that the biological material, e.g., blood or tissue, recognizes the biofunctionalized quantum dots on the device surface as "self" so that an immune or inflammatory response is not stimulated. The coating of foreign surfaces with biofunctionalized quantum dots could be used in a therapeutic, e.g., for coating implants, and in a research context.

EXAMPLE 1

A solution of a glycoside of Formula IV (120 mg) in anhydrous 1,4-dioxane (4 ml) was purged with argon for 20 min. To this solution was added triply distilled thiolacetic acid (1.4 ml) followed by 2,2'-azobisisobutyronitrile (30 mg). The reaction was left to stir under an argon atmosphere at 75° C. for 12 hours and quenched with cyclohexene (0.1 ml). The solution was co-evaporated with xylenes under reduced pressure. Flash column chromatography of the residue on silica gel with a solution of ethyl acetate and hexanes in a volume ratio of 3:1 provided a thioester of Formula V (125 mg).

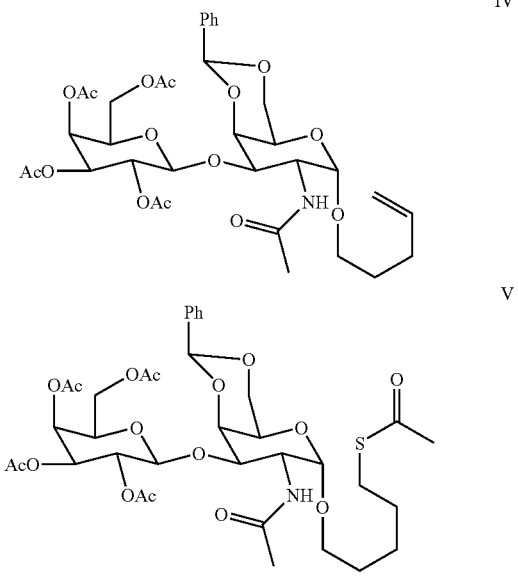

The thioester of Formula V was then debenzylidinated. A first approach for debenzylidination was carried out as follows. The thioester of Formula V (110 mg) was dissolved in a solution of 80% acetic acid in water (3 ml) was stirred at 60° C. for 16 hours. The reaction solution was concentrated at reduced pressure and co-evaporated twice with xylenes. The residue was purified by flash column chromatography on silica gel using a solution of 7% methanol in methylene chloride to provide a debenzylidinated thioester (69 mg).

In a second, alternative approach for debenzylidination, the thioester of Formula V (600 mg) was dissolved in methanol (14 ml) and treated with 3 drops of acetyl chloride. After 30 minutes, the reaction was quenched with pyridine (1 ml) and evaporated. The residue was purified by flash column chromatography using a solvent of 5% to 10% methanol on methylene chloride to yield a debenzylidinated thioester (475 mg).

The debenzylidinated thioester was then hydrolyzed. A first approach for hydrolysis was carried out as follows. A solution of debenzylidinated thioester (30 mg) in methanol (5 ml) was treated with a solution of sodium methoxide in methanol (25% w/v, 25 μl) and allowed to react for 30 minutes. The solution was then neutralized with strongly acidic Amberlite®-120 ion-exchange resin, filtered, and concentrated. Purification was performed on a Strata® SI-1 silica gel cartridge with an eluting solvent of 20% methanol in methylene chloride to yield the Thomsen-Friedenreich-thiol of Formula VI (20 mg) as a white solid.

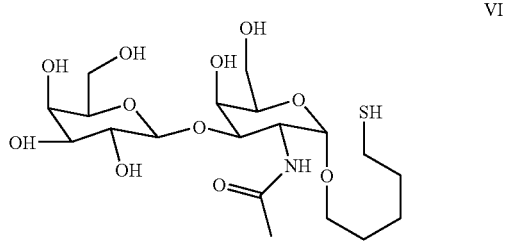

In a second, alternative approach for hydrolysis, the debenzylidinated thioester (300 mg) was dissolved in methanol (5 ml). The solution was treated with a solution of sodium methoxide in methanol (25% (w/v), 30 μl). Air was bubbled through the solution and the solution was stirred at room temperature and allowed to react for 24 hours. The solution was then neutralized with strongly acidic Amberlite®-120, and evaporated under reduced pressure at 50° C. to yield the Thomsen-Friedenreich-disulfide of Formula VII (200 mg). The Thomsen-Friedenreich-disulfide of Formula VII was purified by reverse phase flash chromatography with aqueous methanol to yield purified Thomsen-Friedenreich-disulfide of Formula VII (187 mg) as a white powder which was soluble in water and in methanol. The Thomsen-Friedenreich-disulfide of Formula VII (130 mg) was then dissolved in distilled water (1 ml) and degassed with argon for 20 minutes. Dithiothreitol (130 mg) was added and the solution allowed to react for 20 minutes. The excess dithiothreitol was then removed by several extractions with ethyl acetate. The residue was then purified by reverse phase flash chromatography on a C-18 column with an aqueous solution of methanol (10%-40% (v/v)) to yield the Thomsen-Friedenreich-thiol of Formula VI. The Thomsen-Friedenreich-thiol of Formula VI could be stored under argon at −20° C. without significant dimerization for weeks but normally was used immediately since it oxidizes to the Thomsen-Friedenreich-disulfide of Formula VII upon standing at room temperature.

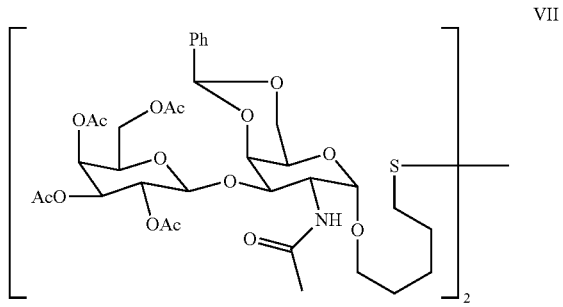

EXAMPLE 2

Hydrogen telluride gas was generated by reacting aluminum telluride ($Al_2Te_3$, 123 mg) with aqueous sulfuric acid (0.5M, 10 ml). The hydrogen telluride was then passed with a slow flow of argon through a deaerated solution of sodium hydroxide in water (50 mM, 10 ml) to yield a solution of hydrogen sodium telluride (NaHTe, 50 mM).

Figure 2:
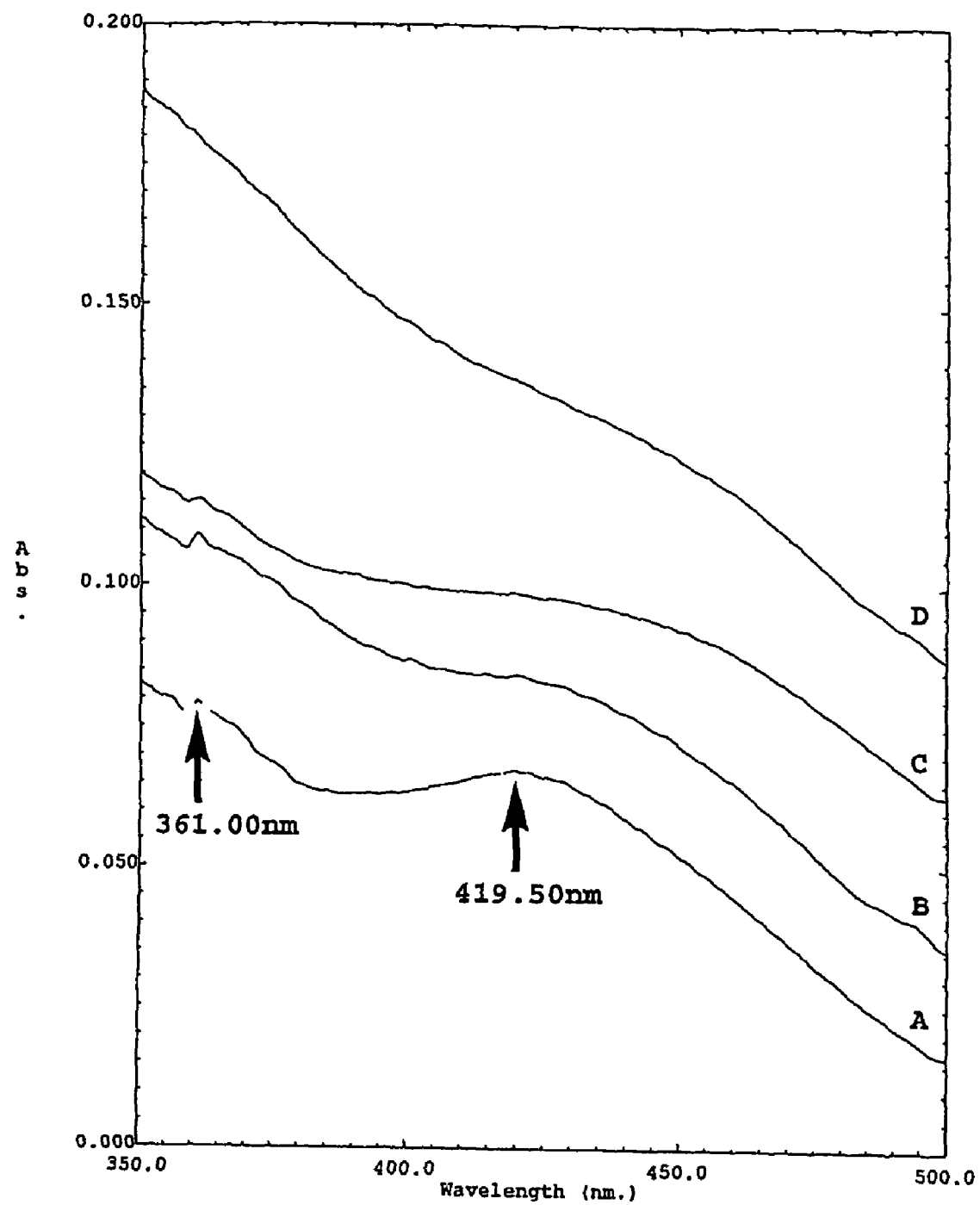
FIG. 2 is a graph of the absorption spectra of growing Thomsen-Friedenreich-functionalized cadmium telluride quantum dots at different times.
Figure 3:
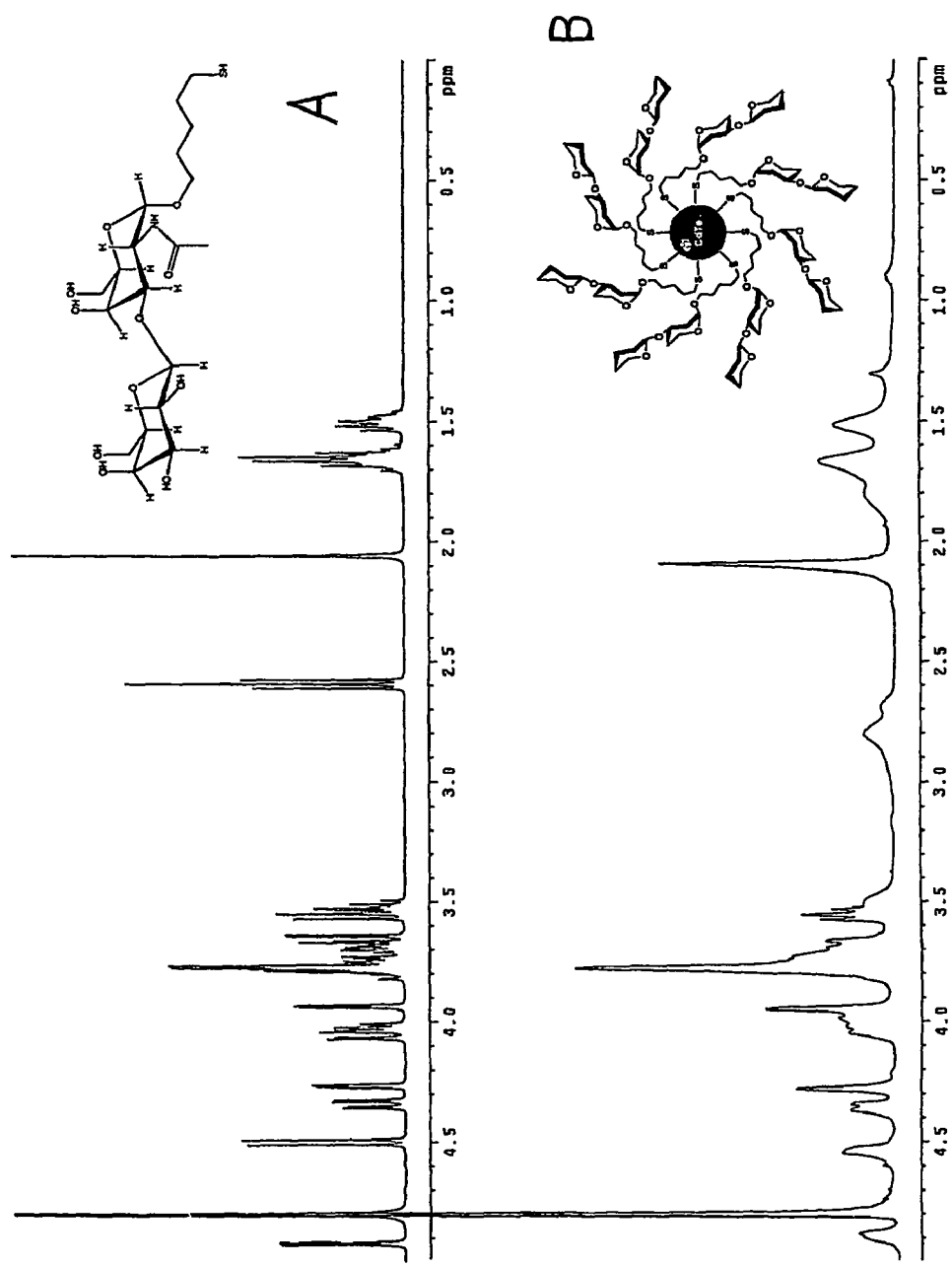
FIG. 3 shows the NMR spectra of a Thomsen-Friedenreich-thiol and of Thomsen-Friedenreich-functionalized cadmium telluride quantum dots.

The Thomsen-Friedenreich-thiol of Formula VI (28 mg) was then dissolved in an aqueous solution of cadmium perchlorate (16 mM, 700 μl) and was purged with argon for 20 minutes. The freshly prepared hydrogen sodium telluride solution (115 μl) was then quickly added to this mixture. The mixture was then refluxed in the open air. During the refluxing, 50 μl aliquots were collected and analyzed for UV absorption. The absorption spectra during the first 2 hours of the synthesis are shown in FIG. 2, in which curve A represents an aliquot taken at 30 minutes, curve B represents an aliquot taken at 60 minutes, curve C represents an aliquot taken at 90 minutes, and curve D represents an aliquot taken at 120 minutes. Rapid growth of the nanocrystals during these first 2 hours is evident from the shift of the absorption maxima to longer wavelengths (see Gaponik et al., J. Phys. Chem. B, (2002) v.106, p. 7177). After 48 hours of refluxing, faint green luminescence was observed. The solution was cooled to ambient temperature, diluted with water, and purified from the low molecular weight impurities on Centriplus® YD-30 (MWCO 30 KDa) cartridges. Drying of the purified solution yielded Thomsen-Friedenreich-functionalized cadmium telluride quantum dots as a pale yellow fluffy substance that was freely soluble in water. Comparison of the $^1$H NMR spectra of the Thomsen-Friedenreich-thiol of Formula VI (label A) and the Thomsen-Friedenreich-functionalized cadmium telluride quantum dots (label B) in deuterium oxide solution is shown in FIG. 3. The absence of sharp peaks in the spectrum of the Thomsen-Friedenreich-functionalized cadmium telluride quantum dots in deuterium oxide indicates that no free ligands are present in solution.

In a modified procedure, the Thomsen-Friedenreich-thiol of Formula VI, the cadmium perchlorate, and the hydrogen sodium telluride solution can be dissolved in N,N-dimethylformamide and the solution can be refluxed.

EXAMPLE 3

Hydrogen telluride gas was generated by reacting aluminum telluride ($Al_2Te_3$, 123 mg) with aqueous sulfuric acid (0.5M, 10 ml). The hydrogen telluride was then passed with a slow flow of argon through a deaerated solution of sodium hydroxide in water (50 mM, 10 ml) to yield a solution of hydrogen sodium telluride (NaHTe, 50 mM).

The Thomsen-Friedenreich-thiol of Formula VI (12.3 mg) and mercaptoacetic acid (3 ml) were dissolved in an aqueous solution of cadmium perchlorate (16 mM, 1400 μl) and purged with argon for 20 minutes. The freshly prepared hydrogen sodium telluride solution (230 μl) was then quickly added to this mixture under argon. The mixture was then refluxed in the open air. Aliquots were taken after 15, 21, 27, and 39 hours; the intensity of fluorescence was observed to increase with time. After 39 hours of refluxing, bright yellow luminescence was observed. The solution was cooled to ambient temperature, diluted with water, and purified from low molecular weight impurities on Centriplus® YD-50 (MWCO 50 KDa) cartridges. Drying of the purified solution yielded Thomsen-Friedenreich-mercaptoacetic-acid-functionalized cadmium telluride quantum dots (4 mg) as a yellow fluffy substance that was freely soluble in water and dimethylsulfoxide.

Figure 4:
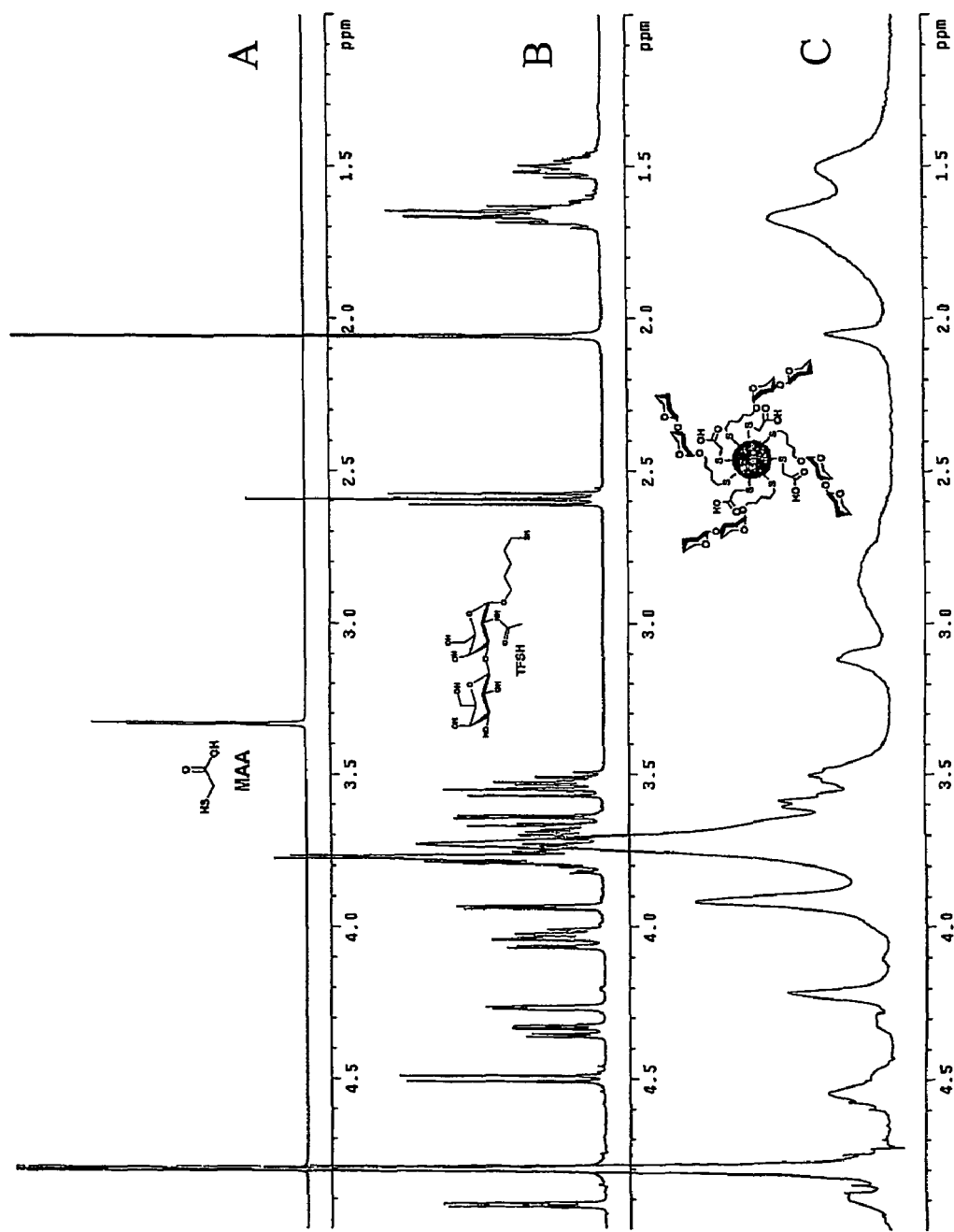
FIG. 4 shows the NMR spectra of mercaptoacetic acid, of a Thomsen-Friedenreich-thiol, and of Thomsen-Friedenreich-mercaptoacetic-acid-functionalized cadmium telluride quantum dots.
Figure 5:
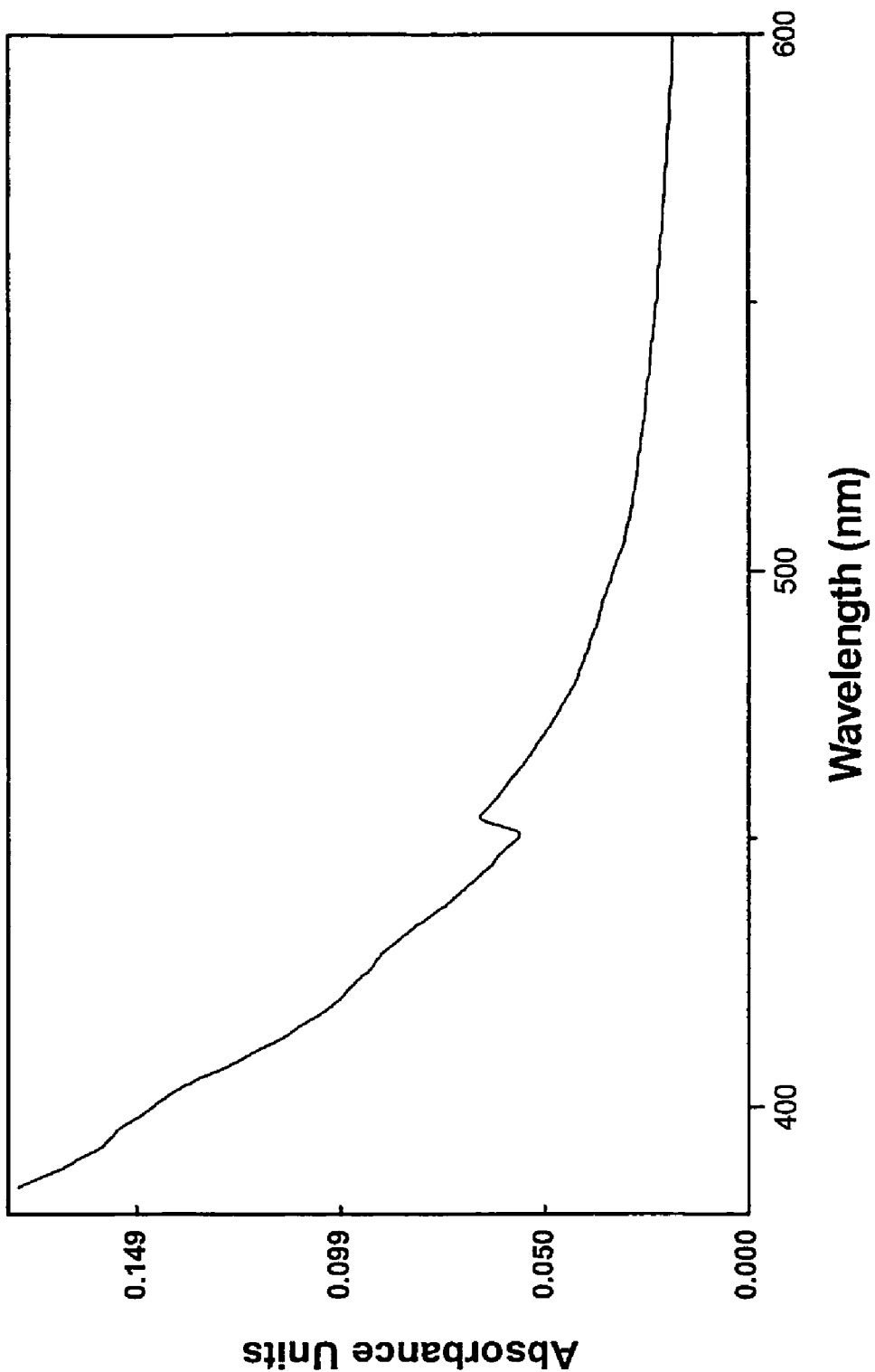
FIG. 5 shows the absorption spectrum of Thomsen-Friedenreich-mercaptoacetic-acid-functionalized cadmium telluride quantum dots.

The $^1$H NMR spectra of mercaptoacetic acid (label A), the Thomsen-Friedenreich-thiol of Formula VI (label B), and the Thomsen-Friedenreich-mercaptoacetic-acid-functionalized cadmium telluride quantum dots (label C) in deuterium oxide solution are shown in FIG. 4. The broad peaks in the spectrum of the quantum dots (label C) are a result of increased relaxation rates due to effective molecular weight (>50 KDa) of the nanoparticles and the close packing of the mercaptoacetic acid and the Thomsen-Friedenreich-thiol groups on their surface. The downfield shift of the —$CH_2S$— methylene triplet (δ 2.6, spectrum B) may be attributed to the close proximity of C—S to the semiconductor surface which results in strong electronic interaction. Interestingly, this methylene signal completely disappeared when the Thomsen-Friedenreich-thiol of Formula VI was attached to gold nanoparticles. The chemical shifts of the remaining protons confirmed that the bonded Thomsen-Friedenreich groups have the same structure as in the free Thomsen-Friedenreich thiol. Also noteworthy is the fact that, although a three-fold excess of the Thomsen-Friedenreich-thiol over mercaptoacetic acid was used in the synthesis, the NMR shows that approximately 1.5 molecules of mercaptoacetic acid were incorporated into a quantum dot per molecule of the Thomsen-Friedenreich-thiol incorporated, as calculated by integration of the methylene signal of mercaptoacetic acid (δ 3.1) and the methyl group on the acetamide group (δ 2.1) of the Thomsen-Friedenreich-thiol. This effect of preferential binding affinity of one ligand over another was reported before in the synthesis of hybrid sugar-bearing gold nanoparticles. See Barrientos et al., Chem. Eur. J, v. 9 (2003) p. 1909. The absence of sharp peaks in the spectrum of the Thomsen-Friedenreich-mercaptoacetic-acid-functionalized cadmium telluride quantum dots in deuterium oxide solution indicates that no free mercaptoacetic acid or free Thomsen-Friedenreich-thiol of Formula VI is present in solution. The absorption spectrum of Thomsen-Friedenreich-mercaptoacetic-acid-functionalized cadmium telluride quantum dots is shown in FIG. 5 in which the first excitonic maximum at 460 nm is apparent.

Coupling between Thomsen-Friedenreich-mercaptoacetic-acid-functionalized cadmium telluride quantum dots and a monoclonal anti-Thomsen-Friedenreich antibody was observed. Imaging with a laser scanning confocal microscope clearly revealed time-dependent aggregation of the quantum dots over time after addition of the antibody. This result confirms that the functional integrity of the Thomsen-Friedenreich antigen is conserved while the antigen is linked to the quantum dot.

The Thomsen-Friedenreich-mercaptoacetic-acid-functionalized cadmium telluride quantum dot samples showed prolonged stability of their luminescence against oxidation. Thus, solutions of pure Thomsen-Friedenreich-mercaptoacetic-acid-functionalized cadmium telluride quantum dots in water stored in the dark at 4° C. for at least 4 months showed no signs of decreased luminescence or precipitation or flocculation. NMR analysis of samples indicated that there was no leaching of the mercaptoacetic acid or Thomsen-Friedenreich groups from the quantum dot into the water. This stability is remarkable. Similarly prepared mercatoacetic acid or mercaptoproprionic acid capped quantum dots, which were not capped with a saccharide group completely flocculated in a few days when stored in aqueous solution in the absence of free ligand.

In a modified procedure, the Thomsen-Friedenreich-thiol of Formula VI, the mercaptoacetic acid, the cadmium perchlorate, and the hydrogen sodium telluride solution can be dissolved in N,N-dimethylformamide and the solution refluxed.

In summary, a simple aqueous synthesis of robust, luminescent tumor-associated-carbohydrate-antigen-encapsulated cadmium telluride quantum dots is reported for the first time.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

What is claimed is:

1. A method for producing a biofunctionalized quantum dot, comprising:

refluxing simultaneously a biofunctional group-thiol of Formula III

and a mercaptoalkanoic acid, a cadmium salt, a hydrogen-alkali-selenide or hydrogen-alkali-telluride, and a suitable solvent to produce a quantum dot in a solution,
wherein $R_1$ comprises a hydrocarbon, and
wherein the biofunctional group comprises a saccharide.

2. The method of claim 1, wherein the refluxing uses a solvent comprising water or N,N-dimethylformamide.

3. The method of claim 1, wherein the biofunctional group-thiol of Formula III is produced by the steps of:

reacting a glycoside of Formula I with an alkylthio acid to produce a thioester of Formula II;

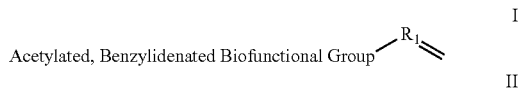

debenzylidenating the thioester of Formula II; and
hydrolyzing the thioester of Formula II to produce a biofunctional group-thiol of Formula III,
wherein $R_1$ comprises a carbon atom and $R_2$ comprises a carbon atom.

4. A method according to claim 1, comprises: providing a biofunctional group-thiol of Formula VI by the steps of:

reacting a glycoside of Formula IV with an alkylthio acid in the presence of 2,2'-azobisisobutyronitrile in 1,4-dioxane at about 75° C. to produce a thioester of Formula V;

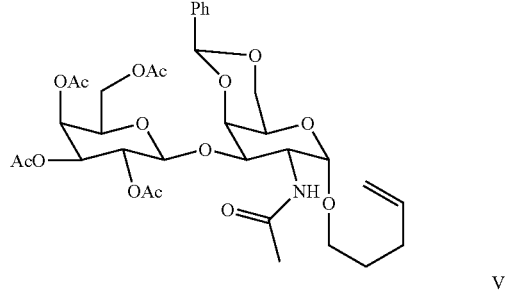

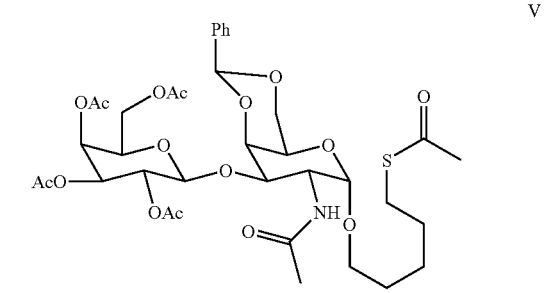

debenzylidinating the thioester of Formula V;
hydrolyzing the debenzylidinated thioester of Formula V to produce a Thomsen-Friedenreich-thiol of Formula VI; and

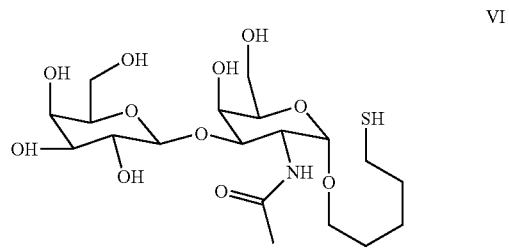

refluxing simultaneously the Thomsen-Friedenreich-thiol of Formula VI with cadmium perchlorate. mercaptoacetic acid, hydrogen sodium telluride, and a suitable solvent, selected from the group consisting of water and N,N-dimethylformamide, to produce a Thomsen-Friedenreich-functionalized quantum dot in a solution.

* * * * *